United States Patent [19]
Bradley et al.

[11] Patent Number: 5,486,474
[45] Date of Patent: Jan. 23, 1996

[54] BIOREMEDIATION METHOD USING A HIGH NITROGEN-CONTAINING CULTURE OF WHITE ROT FUNGI ON SUGAR BEET PULP

[75] Inventors: Clifford A. Bradley; Robert D. Kearns; Pauline P. Wood; William E. Black, all of Butte, Mont.

[73] Assignee: Mycotech Corporation, Butte, Mont.

[21] Appl. No.: 3,836

[22] Filed: Jan. 11, 1993

Related U.S. Application Data

[63] Continuation of Ser. No. 649,438, Feb. 1, 1991, abandoned.
[51] Int. Cl.⁶ ................. C02F 1/00; C02F 3/00; C12N 1/22; C07C 7/00
[52] U.S. Cl. ............ 435/262; 210/606; 210/632; 424/93.5; 435/252; 435/254.1; 435/262.5; 435/264; 435/911
[58] Field of Search ............... 435/252, 254, 435/262, 264, 254.1, 262.5, 911; 47/1.1; 210/606, 632; 424/93.5

[56] References Cited

U.S. PATENT DOCUMENTS

| | | | |
|---|---|---|---|
| 4,554,075 | 11/1985 | Chang et al. | 435/262 |
| 4,711,787 | 12/1987 | Odakra | 426/31 |
| 4,803,800 | 2/1989 | Romaine et al. | 47/1.1 |
| 4,891,320 | 1/1990 | Aust et al. | 435/262 |

OTHER PUBLICATIONS

Kirk et al. (editors), *Lignin Biodegradation: Microbiology, Chemistry and Potential Applications*, vol. 1, CRC Press, p. 215, 1980.
Kirk et al. (editors), *Lignin Biodegradation: Microbiology, Chemistry and Potential Applications*, vol. II, CRC Press, p. 180, 1980.
Ferri, Biological Abstracts, vol. 81, No. 2, Abstract No. 9847, 1986.
Bumpus, Applied and Environmental Microbiology, vol. 55, No. 1, pp. 154–158, 1989.
Fungal Nutrition and Physiology, pp. 81–83 1984.
Rolz, C. et al. *Appl. Microbiol. and Biotechnol.* 25:535–541 (1987).
Agosin, E. amd Odier, E. *Appl. Microbiol. and Biotechnol.* 21:397–403 (1985).
Aitken, M. D. et al. *Wat. Res.* 23(4):443–450 (1989).
Tengerdy, R. P. *Trends in Biotechnology* 3(4):96–99 (1985).
Keyser et al., "Ligninolytic Enzyme System of Phanerochaete chrysosporium: Synthesized in the Absence of Lignin in Response to Nitrogen Starvation", *Journal of Bacteriology*, Sep. 1978, vol. 135, No. 3, pp. 790–797.
Mileski et al., "Biodegradation of Pentachlorophenol by the White Rot Fungus Phanerochaete chrysosporium", *Applied and Environmental Microbiology*, Dec. 1988, vol. 54, No. 12, pp. 2885–2889.
Bumpus, John A., "Biodegradation of Polycyclic Aromatic Hydrocarbons by Phanerochaete chrysosporium", *Applied and Environmental Microbiology*, Jan. 1989, vol. 55, No. 1, pp. 154–158.
Haemmerli et al., "Oxidation of Benzo(a)pyrene by Extracellular Ligninases of Phanerochaete chrysosporium", *The Journal of Biological Chemistry*, 1986, vol. 261, No. 15, pp. 6900–6903.
Roch et al., "Lignin peroxidase production by strains of Phanerochaete chrysosporium grown on glycerol", *Appl. Microbiol. Biotechnol.*, (1989) vol. 31, pp. 587–591.
Kirk et al., "Influence of Culture Parameters on Lignin Metabolism by Phanerochaete chrysosporium", *Arch. Microbiol.*, (1978), vol. 117, pp. 277–285.
Ferri, F. (1984) *Mic. Ital.* 2:27–30 (translation).

*Primary Examiner*—Marian C. Knode
*Assistant Examiner*—Deborah K. Ware
*Attorney, Agent, or Firm*—Lahive & Cockfield

[57] ABSTRACT

A bioremediation method for degrading aromatic compounds using white-rot fungus and a sugar beet pulp substrate having a high nitrogen content is disclosed. The sugar beet pulp substrate has a total nitrogen content based on dry weight of about ten percent. Further the white rot fungus utilized can be taken from several genera, including Phanerochaete, Phlebia, Trametes, Pleurotus and Bjerkandera. Two specific genus species of the white rot fungi useful in the biormeditation method are *Phaneorochaete chrysosporium* and *Bjerkandera adjusta*. The admixture of a white rot fungus and sugar beet pulp solid substrate is capable of enzymatically degrading aromatic compounds. In addition the method is useful for degrading chlorinated aromatic compounds and polynuclear aromatic hydrocarbons in soil and water.

14 Claims, No Drawings

BIOREMEDIATION METHOD USING A HIGH NITROGEN-CONTAINING CULTURE OF WHITE ROT FUNGI ON SUGAR BEET PULP

This application is a continuation of application Ser. No. 07/649,438, filed on Feb. 1, 1991, now abandoned.

BACKGROUND OF THE INVENTION

Enzymes for degrading aromatic compounds have potential commercial application in the pulp and paper industry, the production of fuels and chemicals from lignocellulose, the enhancement of livestock feeds, and the bioremediation of aromatic hazardous wastes.

Lignin is a complex polymer of phenyl propanoid units with a variety of interunit linkages forming a nonlinear, random structure. Lignin comprises 10–35% of the dry weight of lignocellulose-rich materials such as wood, straw, and corn stover. Lignin is resistant to biological destruction, although it is enzymatically degraded by various higher order fungi. In nature, the basidiomycetes that cause white-rot wood decay are major degraders of lignocellulose. White-rot fungi oxidize lignin completely to carbon dioxide. Extracellular enzymes complexes secreted by these fungi catalyze oxidative reactions of the lignin structure. White-rot fungi have also been shown to oxidize and degrade a wide range of other aromatic structures including a variety of man-made, toxic aromatic compounds. The term "white-rot fungi" as used herein is intended to include fungi having enzyme capable of oxidizing and thereby degrading aromatic compounds.

There are an estimated 1700 species of white-rot fungi. However, research on enzymatic lignin degradation has concentrated on one organism: *Phanerochaete chrysosporium*. Lignin-degrading enzymes from this organism have been purified and characterized. A large volume of research literature describes processes for growing *P. chrysosporium* in liquid media for lignin degradation or production of lignin-degrading enzymes. The conventional production of lignin-degrading enzymes in liquid media occurs during secondary metabolism and is initiated by nitrogen or glucose starvation. For instance, in U.S. Pat. No. 4,554,075, Chang et al. describe a process for growing white-rot fungi by carrying growth into secondary metabolism wherein nitrogen starvation occurs. See also Ming Tien in an article in *CRC Critical Reviews in Microbiology*, titled "Properties of Ligninase From Phanerochaete Chrysosporium and Their Possible Applications", Volume 15, Issue 2 (1987) at p. 143 and U.S. Pat. No. 4,891,230 to Aust et al.

The slow growth rates and low cell mass production associated with starved cultures results in long growth times and low yields thus making this impractical for commercially producing enzymes for pretreating wood pulp in paper making processes, for in situ treatment of toxic waste, or for enhancing lignocellulose for livestock feed. Tien notes on page 144 in the same article listed above that scale-up from liquid culture grown in flasks has proven difficult.

To overcome the low cell mass production, the art has suggested growing several species of white-rot fungi using solid culture media in solid state reactors. In these instances, the fungus grows on a substrate of moist solid lignocellulose-containing materials. Straw, several types of wood, and milled corn cob have been disclosed as substrates in the literature. These materials have been selected as culture substrates primarily because they are typical of the materials degraded by the white-rot fungi in nature. They have a relatively high lignin content of 10–35%, low nitrogen levels, and limited access to cellulose as a carbon source. White-rot fungi can be grown in such solid-state cultures, but obtaining lignin-degrading enzymes in cell and solids free extracts of such cultures has proved an elusive task as the enzyme activity remains bound to the substrate.

Several patents as well as other literature disclose processes for preparing ligninase in solid cultures including U.S. Pat. No. 4,711,787 to Odakra, which describes using okra as a substrate for the production of livestock feed. Rolz, et al., in an article in *Applied Microbiology and Biotechnology* titled, "White-Rot Fungal Growth on Sugarcane Lignocellulosic Residue", Volume 25 (1987) pp. 535–541, report using sugarcane residue as a substrate. In U.S. Pat. No. 4,891,320, Aust et al. list as typical materials used to grow white-rot fungi for use in degradation of aromatic compounds shredded paper, wood shavings, sawdust, corn cobs, and humus. None of these references discloses the production of enzymes during the primary metabolic growth phase or the production of cell-free culture extracts containing lignin-degrading enzymes.

It is believed that the reason why extracting cell-free enzymes is difficult in conventional solid state processes for producing enzymes is that the enzymes are absorbed into the lignocellulosic substrate materials. Thus, when using substrates of the type normally associated in nature with white-rot fungi, lignin-degrading enzymes are difficult to extract or purify in active form. These substrates typically have a high lignin content and low protein content. On the other hand, small amounts of cell-free enzymes are present in liquid cultures, presumably because there are no surfaces for enzyme absorption.

Both liquid and solid substrate cultures of white-rot fungi have been the subject of at least 15 years of intensive research in numerous laboratories, as evidenced by the volume of research literature and patents granted in this field. However, the problems of producing enzymes during the primary metabolic growth phase, of producing cell-free enzymes from solid culture and of producing lignin-degrading enzyme preparations with commercially useful enzyme concentrations remain unsolved.

SUMMARY OF INVENTION

This invention pertains to a novel composition of matter comprising a solid state culture of white-rot fungus in a mixture with a substrate comprising as an important ingredient sugar beet pulp. The invention also pertains to use of the fungal culture to degrade aromatic compounds such as lignin or aromatic organic pollutants. The culture also can be used for production of by-products of fungal growth such as lignin-degrading enzymes. The culture advantageously permits the production of lignin-degrading enzymes by the white-rot fungi during the primary metabolic growth phase of the fungus rather than during secondary metabolism. Furthermore, the lignin-degrading enzymes can be separated easily from the substrate material for the production of cell-free enzymes preparations.

The culture is prepared by growing white-rot fungus under growth-supportive conditions on a substrate comprising sugar beet pulp. An inoculum culture of white-rot fungus is prepared for inoculating the substrate. Water and nutrients are added. A substrate of sugar beet pulp is prepared typically by sterilizing the substrate as by autoclaving and then cooling the substrate. The substrate is inoculated with the prepared inoculum. The inoculated substrate is then placed in a solid state reactor for growing fungi, and the mixture is aerated to enhance growth. Nonlimiting examples of white-rot fungi that can be grown in the substrate include species from the genera Phanerochaete, Phlebia, Trametes, Pleurotus, and Bjerkandera.

At the conclusion of the growing period, the culture can be used without further processing. For example, the culture can be used in bioremediation processes to degrade aromatic organic pollutants in a soil or water mass. Alternatively, extracts rich in lignin-degrading enzymes may be separated from the substrate.

For production of by-product of fungal growth, one can isolate by-products from the culture after an appropriate growth period. For example, the substrate can be washed with water to bring aqueous-soluble enzymes such as ligninases into solution. The lignin-degrading enzymes can be recovered separate from the substrate using this process. The enzyme-rich solution can be centrifuged and filtered to provide a cell free liquid enzyme preparation containing lignin-degrading enzymes that have been removed from the substrate.

The growth of white-rot fungi on sugar beet pulp substrate results in the ability to produce lignin-degrading enzymes during the primary metabolic growth phase of the fungus when an abundance of nutrients are available and growth rate is optimal rather than in secondary metabolism with limited nitrogen or carbon. The ability to produce lignin-degrading enzymes commercially during the primary metabolic growth phase and to produce cell free lignin-degrading enzymes is an advantage of this invention over conventional solid state or liquid culture process used to produce these enzymes using white-rot fungi.

DETAILED DESCRIPTION OF THE INVENTION

Sugar beet pulp is used as the substrate material for fungal growth in accordance with this invention. Sugar beet pulp is produced in large amounts and is readily available for high-volume, commercial applications for growing white-rot fungi.

Sugar beet pulp has not been reported as a natural substrate for white-rot fungi. It has a relatively low lignin content of 1% to 3%. White-rot fungi occurs naturally as decay organisms on woody materials with high lignin content such as okra, sugarcane, shredded paper, wood shavings, sawdust, corn cobs and humus. These materials have been used in conventional production of lignin-degrading enzymes.

Sugar beet pulp contains 8–10% protein and up to 5% residual sucrose and is not a carbon and nitrogen limited substrate. Yet, white-rot fungi produce lignin-degrading enzymes when grown on sugar beet pulp during the primary metabolic growth phase. This result is unexpected because production of these enzymes using conventional processes typically occurs only with carbon or nitrogen starvation during the secondary metabolism stage.

Sugar beet pulp is a by-product of the processing of sugar beets for sugar (sucrose). In a typical process, sugar beets are sliced and extracted with hot water to recover the sugar. Sugar beet pulp is the residue of sugar beets remaining after the extraction process. In most sugar beet processing plants, the sugar beet pulp is dried and sold as cattle feed. Sugar beet pulp is composed of the following constituents with the typical proportions shown as a percentage on a dry weight basis.

| Mean chemical composition of raw sugar beet pulp | |
|---|---|
| Components | Raw Pulp |
| Dry matter | 91.5 |
| Total Nitrogen (×6.25) | 10.8 |
| Protein Nitrogen (×6.25) | 9.0 |
| Ashes | 4.3 |
| Organic Matter | 95.7 |
| ADF[a] | 23.3 |
| NDF[b] | 51.9 |
| Lignin | 1.0 |
| Cellulose (ADF-Lignin) | 22.3 |
| Hemicellulose (NDF-ADF) | 28.6 |
| Gross Energy (kcal/kg dry matter) | 4217 |

[a]This is acid detergent fiber.
[b]This is neutral detergent fiber.
*A. Duranl and D. Cherau (1988); "A New Pilot Reactor for Solid State Fermentation: Application to the Protein Enrichment of Sugar Beet Pulp"; Biotechnology and Bioengineering, Vol. 31, pp 476–486.

Particles of sugar beet pulp are typically 0.5 to 1 cm in the largest dimension and irregularly shaped.

Sugar beet pulp can be prepared for use as a solid culture substrate as follows. Dry sugar beet pulp is moistened with one of a number of standard nutrient solutions supportive of fungal growth and then sterilized by autoclaving, e.g., at 125° C., 15 psi for 20 minutes. Other generally accepted methods for sterilization can be used involving different temperatures, pressures, and durations as long as the sugar beet pulp is sterilized before inoculation. The sugar beet pulp is then cooled to between 20°–40° C.

An inoculum of white-rot fungi is then aseptically and thoroughly mixed with the cooled sugar beet substrate. The inoculum can be prepared in any conventional manner such as by first selecting a pure culture of a white-rot fungus and maintaining this fungus on nutrient agar slants. Next, the culture on the agar slants is transferred to either a liquid or solid media and grown at 20°–40° C. The media selected varies somewhat depending upon which organism is selected for growth. If a liquid media is selected for growing the inoculum, the liquid inoculum media should contain glucose, a nitrogen source, and nutrient salts. Liquid cultures can be held stationary or agitated during the culture growth phase. If a solid media is selected for growing the inoculum, either sterilized sugar beet pulp, prepared as described above, or other known materials can be used as a substrate. Generally, sufficient inoculum culture is grown to provide approximately 1–20% by volume of the mass of substrate to be inoculated.

According to this invention, the inoculated sugar beet pulp comprises a solid state culture characterized by a solid phase of particles of sugar beet pulp, an aqueous phase sorbed into the particles of the pulp and a gas phase in the interparticle spaces. Moisture content of the sugar beet pulp is 40 to 80%, typically 66% by weight. Optionally, 2–10% sterilized straw can also be added to the sugar beet pulp. Straw may be added before or, more typically, after the beet pulp is wetted. The straw improves the physical characteristics of the solid culture by increasing the volume and maintaining integrity of interparticle spaces resulting in improved aeration, temperature control, and moisture control.

The fungus grows on the surface of, and penetrates into, the particles of sugar beet pulp.

The inoculated substrate is placed in a vessel designed as a solid culture reactor or in a trench or pile. The shape and dimensions of the vessel used as the solid culture reactor may be varied widely. In one currently developed embodiment, the inoculated substrate is placed in cylindrical or rectangular vessel in a bed approximately 70 cm. deep. The vessel is designed so that air at controlled temperature and humidity can be circulated through the bed and appropriate means are provided for this.

In a solid state reactor, the temperature, nutrients, aeration rate, and growing period can be varied to regulate the metabolic rate of the culture. Metabolic conditions also can determine the species of enzymes grown. Typically, the temperature of the substrate is maintained between 20°–40° C. depending on the organism and enzyme preparation being produced. A nutrient solution may be added to the substrate as necessary to maintain primary metabolic growth phase. Sufficient conventional nutrient solution is provided during the growing period to prevent nitrogen or carbon starvation or secondary metabolism.

An atmosphere of air, or an artificially created atmosphere having an oxygen concentration of 7–100%, is circulated around and through the substrate during the growing period. An aeration rate of between 0.05 to 20 unit volumes of air per minute per unit volume of substrate may be used. The aeration atmosphere preferably is maintained between 70–99% relative humidity. The relative humidity typically is varied to maintain the absorbed water content of the substrate between about 40–80% initially, and then between about 60–80% at the end of the growing period, with 66–72% being typical. The growing period of the culture is varied from 4 to 30 days, depending on the identity of the organism and the type of enzyme under cultivation.

At the completion of the growing period, the culture comprises a fungal cell mass, unutilized culture substrate, and extracellular enzymes. For some applications, particularly in situ degradation of toxic wastes, the whole wet culture may be used without further processing by merely turning the culture into the soil.

To produce a cell-free liquid enzyme preparation containing lignin-degrading enzymes, one can extract the culture by mixing it with water. Alternatively, water together with conventional, biologically compatible detergents, such as TWEEN 80, may be used as an extractant. A solution of cell-free enzymes is extracted from the substrate by centrifuging and filtering such as with a filter having, for example, a 0.8 micron pore size.

The sugar beet pulp substrate is capable of sustaining growth of a variety of white-rot fungi to induce production of at least four types of enzymes, namely, peroxidases, manganese peroxidases, oxidases and laccases. To determine the nature of the enzymes present in various extracts, conventional assay procedures such as those based on enzymatic oxidation of compounds such as phenol red, veratryl alcohol, vanillylacetone and anis alcohol with and without the presence of hydrogen peroxide or oxygen or manganese.

Assays of peroxidase are based on oxidation of phenol red or veratryl alcohol in the presence of hydrogen peroxide. See e.g., Tien, M. (1987) *Critical Review in Microbiology* 15(2):144; Farrell, R., U.S. Pat. No. 4,687,741; Kuwahare, M. et al. (1984) *FEBS Letters* 169(2):247–250; Walder, R. et al. (1988) *Applied Microbiology and Biotechnology* 29:400–407; Tien, M. (1987) *Critical Reviews in Microbiology* 15(2):144; Farrell, R., U.S. Pat. No. 4,687,741. Assays for manganese peroxidase measure oxidation of phenol red, veratryl alcohol or vanillacetone with the presence of both hydrogen peroxide and manganese. See Kuwahare, M. et. al. and Walder, R. et al., supra; Bonnarme, P. and Jefferies, T. W. (1990) *Applied and Environmental Microbiology* 56(1):210–217. Assays for oxidase are based on oxidation of veratryl alcohol or anis alcohol with the presence of oxygen. See Muheim, A. et al. *Enzyme and Microbial Technology;* Walder, R. et al., supra. Assays of laccase activity is based on oxidation of phenol red or 2,6-dimethoxy phenol in the absence of hydrogen peroxide and manganese. See Kuwahare, M. et al. and Walder, R. et al., supra; Haars, A. and Huttermann, A. (1980) *Archives of Microbiology* 125:233–237.

As illustrated in the examples below, culture extracts grown by the processes of this invention have been assayed using each of these procedures. The presence or absence of hydrogen peroxide, manganese, and oxygen in the enzyme reaction provides a basis for distinguishing the different types of activities.

It is an important feature of the invention that all of these different types of enzymes can be produced. Different commercial applications may require specific types or combinations of these types of enzyme activities. Furthermore, the different types of enzymes contained in the white-rot fungus/sugar beet pulp cultures (or in cell-free enzyme preparations derived from these cultures) differ in substrate specificity, pH optima, buffer requirements, and stability. These differences may confer relative advantages from one organism and on one type of enzyme in specific commercial applications.

The cultures of white-rot fungus grown on sugar beet pulp or enzymes extracted from the culture can be used for bioremediation of an aromatic contaminant in a soil or water mass. Soil or water mass containing the contaminant is mixed with the solid state fungal culture or the enzyme extract under conditions which permit the fungal enzymes to degrade at least a portion of the aromatic contaminant. The aromatic contaminants can be halogenated (e.g., chlorinated) aromatic compounds or polynuclear aromatic hydrocarbons.

The invention is illustrated further by the following examples. All percentages are by weight and all inoculum mixture proportions are by volume unless otherwise noted.

EXAMPLE 1

Production of Mn Peroxidase using *P. chrysosporium*

*P. chrysosporium* obtained from the USDA Forest Products Laboratory (strain BKM) was grown without agitation for 10 days at 25° C. in a high-nitrogen, stationary-liquid medium composed of 10 g/l glucose, 5 g/l peptone and 3 g/l yeast extract (Difco). This liquid culture was used as an inoculum culture for the solid culture medium. The solid culture medium consisted of dried sugar beet pulp wetted to 66% moisture with a nutrient solution disclosed in Table 1:

TABLE 1

| TYPICAL NUTRIENT SOLUTION USED | | | |
|---|---|---|---|
| Substance | g/l | Substance | g/l |
| Glucose | 10.0 | $CaCl_2 \cdot 2H_2O$ | .03 |
| $NH_4H_2PO_4$ | .05 | Trace Elements | 5 ml stock solution |
| $KH_2PO_4$ | 1.0 | Veratryl Alcohol | 0 or .14 |
| $MgSO_4 \cdot 7H_2O$ | 1.0 | Peptone | .05 |
| | | Yeast extract | .05 |

The wetted sugar beet pulp was autoclaved at 20° C., 15 psi, for 20 minutes, cooled, and inoculated at the rate of 10 ml inoculum cultures per 100 ml of sugar beet pulp substrate. The solid culture was incubated for 5 days at 28° C. with an air flow of 0.2 volume of air per volume of culture per minute with the air at 90% relative humidity. At 5 days, the culture was extracted by adding 3 volumes of water per one part wet weight of whole culture, blended for one minute, centrifuged, and passed through a 0.8 micron filter to produce a cell and solids-free, liquid enzyme preparation. The extracted enzyme preparation was assayed using the phenol red and vanillylacetone assays. In the presence of both hydrogen peroxide and manganese, activity was 80 Phenol Red Units per ml as assessed by the phenol red assay and 0.92 International Units per ml by vanillylacetone assay. Mn peroxidase was the only activity detected in this preparation. "Phenol Red Units" may be defined as a 0.1 absorbance change in the optical density of a standardized assay. An "International Unit" may be defined as the production of 1 μmole of reaction product per minute using conventional assay techniques such as those exploiting veratryl alcohol, anis alcohol, and vanillylacetone.

EXAMPLE 2

Production of Mn peroxidase and laccase using *P. chrysosporium*

*P. chrysosporium* was grown under the conditions described in Example 1, except that the inoculum volume was 5%, and the dry sugar beet pulp was wetted to 66% moisture with a nutrient solution including 10 g/l glucose, 5 g/l peptone, and 3 g/l yeast extract. Cultures were grown for 14 days and extracted with two volumes of water per 1 volume wet weight culture.

Extracts which were assayed with phenol red contained 62 Phenol Red Units per ml of Mn peroxidase activity and 27 Phenol Red Units per ml of laccase activity.

EXAMPLE 3

Pilot scale production of Mn peroxidase

Cultures were grown under conditions described in Example 1 except that 5% by weight (dry basis) milled straw was added to the sugar beet pulp preparation. Cultures were grown in a 20 liter vessel with a substrate bed depth of 70 cm, aerated with 1 volume air per volume of culture per minute at 27–30° C. Extracts of cultures harvested at 10 days showed Mn peroxidase activity at 56 Phenol Red Units.

EXAMPLE 4

Production of peroxidase, Mn peroxidase and laccase/oxidase using *T. versicolor*

An inoculum culture of *Trametes versicolor* (ATCC 48424) was grown in stationary culture in the salts solution of Example 1 at 27° C. for 7 days. The inoculum culture was used to inoculate (5% v/v) a series of identical solid cultures composed of sugar beet pulp wetted to 66% moisture with the high nitrogen solution of Example 2. Each of the cultures were incubated at 27° C. with an air flow of 0.2 vol/vol culture per minute at 90% RH. These identical solid cultures were extracted in 4 volumes of water at different time intervals and assayed for enzyme activity using phenol red. Results are shown below:

| Culture Time in Days | Phenol Red Units of Mn Peroxidase | Phenol Red Units of Peroxidase | Phenol Red Units of Laccase/Oxidase |
|---|---|---|---|
| 10 | 20 | 18 | 0 |
| 17 | 25 | 17 | 44 |
| 24 | 86 | 37 | 107 |

Laccase/oxidase activity is oxidation of phenol red without hydrogen peroxide or manganese. Assay techniques used in this example do not distinguish between laccase and oxidase type activities.

An additional type of enzyme activity may be produced by growing *Trametes versicolor* according to the method of this example. This is an activity that oxidizes phenol red in the presence of manganese but without hydrogen peroxide. This activity is present in 10 day cultures at 12 Phenol Red Units per ml extract and in 17 day cultures with 47 Phenol Red Units per ml.

EXAMPLE 5

Production of Mn peroxidase and peroxidase using *T. versicolor*

Cultures were grown and extracted under the conditions described in Example 4 except that the inoculum nutrient solution was 10 g/l glucose, 5 g/l peptone and 3 g/l yeast extracts instead of the salts solution. At 10 days culture the extracts contained Phenol Red Units of Mn peroxidase activity and 33 Phenol Red Units of peroxidase activity per ml. Extracts showed no laccase or oxidase activities.

EXAMPLE 6

Pilot scale production of Mn peroxidase and peroxidase using *T. versicolor*

Cultures were grown under conditions described in Example 4 except that 3% by weight (dry basis) milled straw was added to the sugar beet pulp preparation. Cultures were grown in a 20 liter vessel with substrate bed depth of 70 cm., aerated with 1 volume of air per volume of culture per minute. Temperature was maintained at 27°–30° C. Extracts of cultures were made at 10 days with 2 volumes of water per volume wet weight of culture. Extracts contained 37 Phenol Red Units per ml Mn peroxidase, 72 Phenol Red Units per ml peroxidase, and 27 Phenol Red Units per ml laccase/oxidase activity by phenol red assay.

EXAMPLE 7

Production of Mn peroxidase using *P. tremellosus*

Inoculum cultures of *Phlebia tremellosus* were grown at 27° C. for 14 days in unagitated high nitrogen liquid media. Sugar beet pulp was wetted to moisture with the nutrient solution shown below:

| | |
|---|---|
| $NH_4H_2PO_4$ | .2 |
| $KH_2PO_4$ | 2.72 |
| $Mg\ SO_4.7H_2O$ | .5 |
| $CaCl_2$ | .1 |
| Yeast Extract | .05 |
| Thiamine | .001 |
| Veratryl Alcohol | .10 |
| Trace Elements | 5.0 ml |

-continued

| | |
|---|---|
| Glucose | 10 g/l |

Three cultures were grown in this experiment. The first with the nutrient solution, the second with the nutrient solution supplemented with an additional 20 g/l glucose, and the third supplemented with an additional 20 g/l glucose plus 5 g/l peptone and 3 g/l yeast extract. Cultures were grown for 12 days, at 27° C., with 0.2 volumes of 90% RH air per volume of culture per minute. Cultures were extracted with 2 volumes of water per volume wet weight culture. Extracts of all three cultures contained high levels of Mn peroxidase activity in phenol red assay as shown below:

| Culture Medium | Phenol Red Units of Mn Peroxidase |
|---|---|
| Salts | 10 |
| Salts plus glucose | 25 |
| Salts plus glucose, peptone and yeast extract | 78 |

Mn peroxidase was produced regardless of glucose or nitrogen concentration and was the only activity detected.

EXAMPLE 8

Production of peroxidase and Mn peroxidase using *B. adjusta*

Inoculum cultures of *Bjerkandera adjusta* (CBS 595.78) were grown for four days at 28° C. in an agitated nutrient solution comprising 10 g/l glucose, 5 g/l peptone and 3 g/l yeast extract. Sugar beet pulp was wetted to 70% moisture with the same high nitrogen media and inoculated at 10% v/v with the inoculum culture. Inoculated sugar beet pulp was incubated for 10 days at 27° C. with an air flow of 0.2 volumes of air per volume of culture per minute with the air at approximately 90% relative humidity.

After 10 days, extracts were made with the addition of three volumes of water per volume wet weight culture by the method of Example 1. Extracts were assayed for peroxidase, Mn peroxidase, and oxidase using phenol red. The extracts contained 47 Phenol Red Units per ml Mn peroxidase and 45 Phenol Red Units per ml peroxidase. Extracts showed no oxidase or laccase activity.

EXAMPLE 9

Production of Mn peroxidase using *B. adjusta*

*B. adjusta* was grown, extracted, and assayed as described in Example 8, except cultures were grown at 20° C. Extracts were made at 14 days culture time. Assays showed 101 Phenol Red Units per ml Mn peroxidase. Extracts also showed manganese peroxidase activity as assessed by veratryl alcohol assay at 0.43 International Units/ml. Extracts showed no oxidase or laccase activity.

EXAMPLE 10

Production of peroxidase using *B. adjusta*

*B. adjusta* was grown and extracted as described in Example 8 except that extracts were made at 12 days culture time. Extracts contained 98 Phenol Red Units per ml peroxidase activity by phenol red assay. Extracts showed no Mn peroxidase, oxidase or laccase activity.

EXAMPLE 11

Production of aryl alcohol oxidase using *B. adjusta*

*Bjerkandera adjusta* was grown under the same conditions as Example 8, except that the sugar beet pulp preparation was wetted with water and the culture grown for 14 days at 30° C. Aqueous extracts contained aryl alcohol oxidase as demonstrated by assay using anis alcohol and veratryl alcohol.

Extracts showed no manganese or hydrogen peroxide dependent activity in these assays. Oxidase activity was 0.667 International Units per ml of extract by anis alcohol assay and 0.30 International Units per ml by veratryl alcohol assay.

EXAMPLE 12

Production of peroxidase using *B. adjusta*

*Bjerkandera adjusta* was grown under the same conditions as Example 8 except that 5% milled barley straw was added to the sugar beet pulp and the culture was grown in a 20 liter vessel aerated with 1 volume of air per volume of culture per minute in a 70 cm. deep substrate bed. Extracts of cultures at 10 days showed peroxidase activity assayed using phenol red. Activity was 56.5 Phenol Red Units per ml.

EXAMPLE 13

Degradation of chlorinated herbicides using cultures of *B. adjusta* grown on sugar beet pulp Soil contaminated with chlorinated herbicides 2,4-dichlorophenoxyacetic acid (2,4-D) and 2,4,5-Trichlorophenoxyacetic acid (2,4,5-T) was decontaminated using a culture of *B. adjusta* grown on sugar beet pulp. The contaminated site is in Joliet, Montana. Contaminated soil is under the raised wooden floor of a building used to store herbicides. The building and the floor prevented any photodegradation of the chlorinated compounds from taking place.

Inoculum cultures of *B. adjusta* were produced as described in example 8 and used to inoculate 5 liter volumes of sugar beet pulp substrate prepared as in example 8. Inoculated substrate was placed in 10 liter vessels in a 10 cm. deep bed and incubated for 10 days at 22–25° C. with a flow of 1 volume of air per volume per volume of culture per minute at approximately 10% RH.

After 10 days, three separate cultures were pooled, transported to the site and mixed with soil. A volume of culture equal to 18% of the volume of soil was used in Plot 1 while a volume of culture equal to 4% of the soil was used in Plot 2. Each plot was approximately one meter square with contamination extending down one meter. The concentration of contaminants was different in the two plots. Soil was treated to a depth of approximately 13 cm. through rototilling. Treated soil was sprayed lightly with water as necessary to maintain soil moisture. A third plot was used as a control plot. No fungus was applied to this plot.

Samples of contaminated soil were removed from the two treatment plots prior to addition of the fungus. A soil sample was also taken from the control plot at this time. Final soil samples were taken 74 days later. Soil samples were analyzed for chlorinated herbicides by an EPA approved laboratory using standard EPA method 8150. Laboratory results are shown in the table below:

| CONCENTRATION IN PPM | | | |
|---|---|---|---|
| Plot ID | Contaminant | Initial Conc. | Final Conc. |
| Plot 1 | 2,4-D | 1,100.00 | 680.0 |
| Plot 2 | 2,4-D | 680.00 | 4.4 |
| Control | 2,4-D | 320.00 | 370.0 |
| Plot 1 | 2,4,5-T | 12.0 | 13.0 |
| Plot 2 | 2,4,5-T | .1 | 1.3 |
| Control | 2,4,5-T | 370.0 | 390.0 |

EXAMPLE 14

Degradation of chlorinated herbicides using cultures of P. Chrysosporium grown on sugar beet pulp Soil contaminated with chlorinated herbicides 2,4-dichlorophenoxyacetic acid (2,4-D) and 2,4,5-Trichlorophenoxyacetic acid (2,4,5-T) was decontaminated using a culture of P. chrysosporium grown on sugar beet pulp. Chlorinated dioxins were also present in the soil and most likely were a by-product of the 2,4,5-T manufacture. The contaminated site is in Joliet, Mont. Contaminated soil is under the raised wooden floor of a building used to store herbicides. The building and the floor prevented any photodegradation of the chlorinated compounds from taking place.

Inoculum cultures of P. chrysosporium were produced as described in example 2 and used to inoculate 5 liter volumes of sugar beet pulp substrate prepared as in example 1. Inoculated substrate was placed in 10 liter vessels in a 10 cm. deep bed and incubated for 6 days at 22°–25° C. with a flow of 1 volume of air per volume per volume of culture per minute at approximately 10% RH.

After 6 days, two separate cultures were pooled, transported to the site and mixed with soil. A volume of culture equal to 18% of the volume of soil was used in Plot 3. The plot was approximately one meter square with contamination extending down one meter. Soil was treated to a depth of approximately 13 cm. through rototilling. Treated soil was sprayed lightly with water as necessary to maintain soil moisture. An untreated plot was used as a control plot.

Samples of contaminated soil were removed from the treated plot prior to addition of the fungus. A soil sample was also taken from the control plot at this time. Final soil samples were taken 74 days later. Soil samples were analyzed for chlorinated herbicides and dioxins using EPA approved laboratories using standard EPA methods. Herbicides were analyzed for using Method 8150 while dioxins were analyzed for using an EPA approved method incorporating Low Resolution Mass Spectrometry. Laboratory results are shown in the following tables:

| CHLORINATED HERBICIDES | | | |
|---|---|---|---|
| | Concentration in ppm | | |
| Plot ID | Contaminant | Initial Conc. | Final Conc. |
| Plot 3 | 2,4-D | 1,100 | 17 |
| Control | 2,4-D | 320 | 340 |
| Plot 3 | 2,4,5-T | 12 | 0.26 |
| Control | 2,4,5-T | 370 | 390 |

Site Demonstration Dioxin Results

| CHLORINATED HERBICIDES | | | |
|---|---|---|---|
| Dioxin Compound | Starting Conc. | Final Conc. | Detection Limit |
| TCDD (total) | 0.16 ppb | N.D. | .090 |
| PeCDD | <0.10 | N.D. | .090 |
| HxCDD | <0.13 | N.D. | .012 |
| HpCDD | 0.88 | 0.079 | .021 |

EXAMPLE 15

Degradation of polynuclear aromatic hydrocarbons (PAH) in creosote contaminated soils using cultures of P. chrysosporium grown on sugar beet pulp Cultures of P. chrysosporium grown on sugar beet pulp were prepared as described in Example 1. At the time the cultures were mixed with the contaminated soil, the cultures contained 30.7 units per gram wet weight of Mn Peroxidase activity assayed using phenol red.

The soil was obtained from a site contaminated with creosote. 50 g soil samples were placed in one liter bottles. Fungal cultures were mixed in with the soil samples at 25, 50, and 75% volume of fungus to volume of soil. The soil samples were incubated for either 30 or 45 days at room temperature. After either 30 or 45 days, depending on the sample, the entire sample of soil and fungal culture was extracted and analyzed. EPA method 8100 for analysis of PAH was used. Concentrations of the four principal PAH compounds are shown in the following table:

| Constituent | Untreated | 25% | 50% | 75% | Time |
|---|---|---|---|---|---|
| Naphthalene* | 2500 ppm | 50 ppm | 50 ppm | 50 ppm | 30 d. |
| Acetnaphthene | 65000 | 29000 | 20000 | 20000 | 30 |
| Fluorene | 42000 | 26000 | 16000 | 10000 | 30 |
| Anthracene | 14500 | 600 | 550 | 700 | 30 |
| Naphthalene* | 2500 | 50 | 50 | 55 | 45 d. |
| Acetnaphthene | 65000 | 14000 | 9000 | 10000 | 45 |
| Fluorene | 42000 | 12000 | 6500 | 6500 | 45 |
| Anthracene | 14500 | 150 | 175 | 160 | 45 |

*When fungal growth substrate is extracted prior to fungal growth and run on the G.C. using the PAH program, this peak occurs at the same time and magnitude as Naphthalene. Florosil does not totally remove it. All PAH analysis of soil/solid fungal inoculum mixtures indicate naphthalene at approximately 50 ppm. However it is unlikely that it is naphthalene in the soil. Additional analysis will be required to determine what this compound is.

Gas chromatography of the untreated control and of the 25 and 50% volume treatments after 45 days incubation was performed. Treated samples showed significant reductions in PAH concentration as indicated by the reduced number and area of the chromatographic peak.

EXAMPLE 16

Degradation of polynuclear aromatic hydrocarbons (PAH) in water using cell-free extracts of Phanerochaete chrysosporium, sugar beet pulp cultures Cultures of P. chrysosporium grown on sugar beet pulp were prepared as described in Example 1. Cultures were extracted by adding 2 volumes of water per one part weight of culture. The culture and water were blended for one minute, centrifuged, and filtered through a 0.8 micron filter. The cell-free, solids-free, filtrate contained 30.7 units per ml.

of Mn. Peroxidase activity as determined by phenol red assay. 20 ml samples of creosote contaminated water were dispensed to reaction vials. 0.5 g, 2.0 g, or 3.0 g of culture extract was added to duplicate samples and the vials sealed. Three contaminated water samples were not mixed with culture extract. These samples were the controls. After 12 hours of incubation at room temperature, the controls and treated water samples were extracted and analyzed for PAH concentration using EPA method 610.

Concentrations of PAH in untreated and treated samples are shown below:
20 gram water samples; white-rot fungi—liquid enzyme extracts
2 hour treatment time
GC Analysis: EPA Method 610

| Fungus Strain - *P. chrysosporium* | | | | |
|---|---|---|---|---|
| | Liquid enzyme dose | | | |
| | 0 | 0.5 g. | 2.0 g. | 3.0 g. |
| compound | concentration in micrograms/liter | | | |
| Acenaphthene | 70 | 53.7 | 37.6 | 15.4 |
| Fluorene | 45 | 27 | 23.1 | 12.1 |
| Phenanthrene | 23 | 11.8 | 13.9 | 4.3 |

EXAMPLE 17

Degradation of polynuclear aromatic hydrocarbons (PAH) in water using cell-free extracts of *Bjerkandera adjusta*, sugar beet pulp cultures Cultures of *B. adjusta* grown on sugar beet pulp were prepared as described in Example 8. Cultures were extracted by adding 2 volumes of water per one part weight of culture. The culture and water were blended for one minute, centrifuged, and filtered through a 0.8 micron filter. The cell-free, solids-free, filtrate contained 95.1 units per ml. of Mn. Peroxidase activity as determined by phenol red assay. 20 ml samples of creosote contaminated water were dispensed to reaction vials. 2.0 g or 5.0 g of culture extract was added to duplicate samples and the vials sealed. Three contaminated water samples were not mixed with culture extract. These samples were the controls. After 12 hours of incubation at room temperature, the controls and treated water samples were extracted and analyzed for PAH concentration using EPA method 610.

Concentrations of PAH in untreated and treated samples are shown below:
20 gram water samples; white-rot fungi - liquid enzyme extracts
12 hour treatment time
GC Analysis: EPA Method 610

| Fungus Strain - *B. Adusta* | | | |
|---|---|---|---|
| | Liquid enzyme dose | | |
| | 0 | 2.0 g. | 5.0 g. |
| compound | concentration in micrograms/liter | | |
| Acenaphthene | 70 | 70 | 0 |
| Fluorene | 45 | 31.6 | 31.6 |
| Phenanthrene | 23 | 25 | 26 |

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. A bioremediation method for degrading at least one aromatic compound in soil or water, comprising:
   a. combining a white-rot fungus and a sugar beet pulp substrate in a high nitrogen fungal culture such that ligninases are produced during primary metabolism romping a ligninase-producing white-rot fungal culture; and
   b. mixing the ligninase-producing white-rot fungal culture with the soil or water containing said at least one aromatic compound at a concentration and temperature sufficient to degrade enzymatically at least a portion of the aromatic compound in the soil or water.

2. The method of claim 1, wherein the at least one aromatic compound is a chlorinated aromatic compound.

3. The method of claim 1, wherein at least one aromatic compound is a polynuclear aromatic hydrocarbon.

4. The method of claim 3, wherein at least one aromatic compound is a mixture of polynuclear aromatic hydrocarbons.

5. The method of claim 1, wherein the white-rot fungus is selected from the group of genera consisting of Phanerochaete, Phlebia, Trametes, Pleurotus and Bjerkandera.

6. The method of claim 5, wherein the white-rot fungus is selected from the group consisting of *P. chrysosporium* and *B. adjusta*.

7. A bioremediation method for degrading at least one aromatic compound in soil or water, comprising:
   mixing a fungal culture with the soil or water containing at least one aromatic compound such that ligninase is produced by the fungal culture thereby degrading enzymatically at least a portion of the aromatic compound in the soil or water, said fungal culture comprising a ligninase-producing white-rot fungus in admixture with a solid substrate containing sugar beet pulp, wherein the white-rot fungus produces ligninase during primary metabolism and the sugar beet pulp substrate has a total nitrogen content based on dry weight of about ten percent.

8. The method of claim 7, wherein the white-rot fungus is selected from the group of genera consisting of Phanerochaete, Phlebia, Trametes, Pleurotus and Bjerkandera.

9. The method of claim 7, Wherein the white-rot fungus is selected from the group consisting of *P. chrysosporium* and *B. adjusta*.

10. The method of claim 7, wherein the at least one aromatic compound is a chlorinated aromatic compound.

11. The method of claim 10, wherein at least one aromatic compound is a polynuclear aromatic hydrocarbon.

12. The method of claim 11, wherein at least one aromatic compound is a mixture of polynuclear aromatic hydrocarbons.

13. A bioremediation method for degrading at least one chlorinated aromatic compound or polynuclear aromatic hydrocarbon in soil or water, the method comprising the step of
   mixing with the soil or water containing the at least one aromatic compound a fungal culture comprising ligninase-producing *P. chrysosporium* in admixture with a solid substrate comprising sugar beet pulp at a concentration sufficient to degrade enzymatically at least a portion of the chlorinated aromatic compound or the polynuclear aromatic hydrocarbon in the soil or water, wherein *P. chrysosporium* produces ligninase during primary metabolism and the sugar beet pulp substrate has a total nitrogen content based on dry weight of about ten percent.

14. A bioremediation method for degrading at least one chlorinated aromatic compound or polynuclear aromatic hydrocarbon in soil or water, the method comprising the step of mixing with the soil or water containing the step of one aromatic compound a fungal culture comprising ligninase-producing *B. adjusta* in admixture with a solid substrate comprising sugar beet pulp at a concentration and temperature sufficient to degrade enzymatically at least a portion of the chlorinated aromatic compound or the polynuclear aromatic hydrocarbon in the soil or water, wherein the *B. adjusta* produces ligninase during primary metabolism and the sugar beet pulp substrate has a total nitrogen content based on dry weight of about ten percent.

* * * * *

UNITED STATES PATENT AND TRADEMARK OFFICE
CERTIFICATE OF CORRECTION

PATENT NO. : 5,486,474
DATED : January 23, 1996
INVENTOR(S) : Bradley et al.

It is certified that error appears in the above-indentified patent and that said Letters Patent is hereby corrected as shown below:

At column 14, line 13, delete "romping" and insert --forming--.

At column 14, line 49, delete "Wherein" and insert --wherein--.

Signed and Sealed this

Sixteenth Day of September, 1997

Attest:

BRUCE LEHMAN

*Attesting Officer*   *Commissioner of Patents and Trademarks*